United States Patent [19]

Aebli et al.

[11] Patent Number: 4,886,887
[45] Date of Patent: Dec. 12, 1989

[54] PROCESS FOR THE PREPARATION OF INDOLINES

[75] Inventors: Beat M. Aebli, Basle; Claude Gremmelmaier, Aesch, both of Switzerland

[73] Assignee: Ciba-Geigy Corporation, Ardsley, N.Y.

[21] Appl. No.: 917,346

[22] Filed: Oct. 9, 1986

Related U.S. Application Data

[63] Continuation-in-part of Ser. No. 796,358, Nov. 8, 1985, abandoned, and a continuation-in-part of Ser. No. 884,836, Jul. 11, 1986, abandoned.

[51] Int. Cl.$^4$ ........................................... C07D 209/08
[52] U.S. Cl. ................................................... 548/490
[58] Field of Search .......................................... 548/490

[56] References Cited

U.S. PATENT DOCUMENTS 2,283,172  5/1942  Bates ..................................... 502/76
2,283,173  5/1942  Bates ..................................... 502/76

FOREIGN PATENT DOCUMENTS 162015   11/1985  European Pat. Off. .
606027   11/1934  Fed. Rep. of Germany .
52-108969  9/1977  Japan .
58-146562  9/1983  Japan .
1394373    5/1975  United Kingdom .
1394374    5/1975  United Kingdom .

OTHER PUBLICATIONS

Ciba-Geigy, Derwent Abstract of European Patent 162,015, published Nov. 21, 1985.
J. Parera, Chem. Abstracts 85:192148(d) (1976).
J. Bakke, H. Heikman and E. B. Hellgren, Acta Chemica Scandinavica B, 28 (1974), pp. 393-398, A New One Step Indole Synthesis.
Industrial and Engineering Chemistry, vol. 41 (1949), 2564-2572.
J. De Boer et al., Chem. Abstr. 72:115231e (1970).
F. Figueras Roca et al., Chem. Abstr. 70:109478h (1969).
Derwent and Japio Abstracts of Japanese Patents J 58-146563 (1983) and J 52-108969 (1977).
Derwent Abstract of Japanese Patent J 58-146562 (1983).
J. H. De Boer and W. J. Visseren, vol. 73 (1970), pp. 1-9.
F. Figueras Roca, L. DeMourgues and V. Trambouze, vol. 14, 107-113 (1969).

Primary Examiner—Mary E. Ceperley
Attorney, Agent, or Firm—Kevin T. Mansfield; Edward McC. Roberts

[57] ABSTRACT

Indolines of the formula

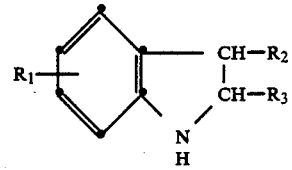

wherein $R_1$ is hydrogen or $C_1$-$C_4$ alkyl and each of $R_2$ and $R_3$ independently of the other is hydrogen, $C_1$-$C_4$ alkyl or phenyl, are prepared by cyclodehydrating a 2-(2'-aminophenyl)ethanol of formula

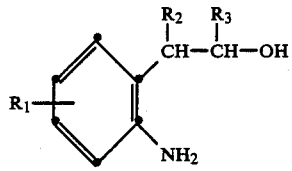

wherein $R_1$, $R_2$ and $R_3$ are as defined above, at 150°-350° C. in the presence of an amorphous aluminum silicate.

The indolines of the above formula are useful intermediates for the synthesis of plant protective agents.

23 Claims, No Drawings

PROCESS FOR THE PREPARATION OF INDOLINES

This is a continuation-in-part of Ser. No. 796,358, filed Nov. 8, 1985, now abandoned and of Ser. No. 884,836, filed July 11, 1986, now abandoned.

The present invention relates to a process for the preparation of indolines of the formula

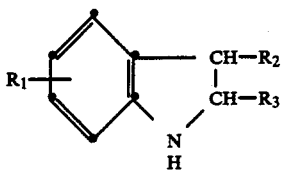

wherein $R_1$ is hydrogen or $C_1$-$C_4$alkyl and each of $R_2$ and $R_3$ independently of the other is hydrogen, $C_1$-$C_4$alkyl or phenyl, by cyclodehydrating a 2-(2'-aminophenyl)ethanol of the formula

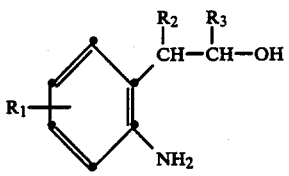

wherein $R_1$, $R_2$ and $R_3$ are as defined for formula I, in the presence of a catalyst.

The indolines of formula I are intermediates for the synthesis of pyrrolo[3,2,1-i,j]quionlines which have bactericidal and fungicidal properties and which may be used for controlling plant diseases. Such pyrrolo[3,2,1-i,j]quinolines are disclosed e.g. in British patent specification Nos. 1 394 373 and 1 394 374. A typical representative of this class of compound to be singled out for special mention is 4-lilolidone (1,2,5,6-tetrahydro-4H-pyrrolo[3,2,1-i,j]quinolin-2-one) of formula III

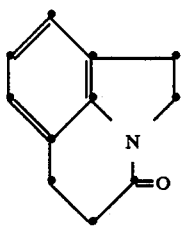

which is also known under the generic name pyroquilon.

From German patent specification 606 027 it is known to prepare indoline by heating 2-(2'-aminophenyl)ethanol, in the gaseous phase in the presence of a condensing agent, to 150°-500° C., in particular from 200°-400° C. The oxides of aluminium, titanium, zirconium, chromium, thorium or mixtures of said oxides are cited as examples of suitable condensing agents. The above mentioned patent specification further teaches that other compound such as sulfates, phosphates, silicates, hydrosilicates, borates, chlorides, mineral acids and acid anhydrides may also be used as condensing agents, either instead of the cited oxides or in admixture with them.

The preparation of indoline by passing gaseous 2-(2'-aminophenyl)-ethanol and hydrogen over silica gel at 250° C. is known from Acta Chem. Scand. B 28 (1974), 393-398. The yield obtained in this process is give as 98%. This process is disadvantageous in that silica gel loses its catalytic activity already after a short time. Therefore, the process is not appropriate fro an economic production of indoline on industrial scale.

Further, it is known to produce indolines by cyclodehydrating corresponding 2-(2'-aminophenyl)-ethanols in the liquid phase. Thus Japanese patent application No. Sho-52-108.969 describes a process in which indolines are prepared by simple heating of 2-(2'-aminophenyl)ethanol to 200°-300° C. in an apparatus made of pyrex glass, and wherein the pressure prevailing during the reaction is so chosen that the 2-(2'-aminophenyl)ethanol remains at least to some degree fluid. By carrying out this process at a reaction temperature of 250° C. and after a reaction time of 2 hours, starting from 2-(2'-aminophenyl)ethanol, the yield of indoline is said to be 99% of theory and, at a reaction temperature of 260° C. and after a reaction time of 6 hours, starting from substituted indoline is said to be 77-94% of theory. These particulars on the obtainable yields, however, were not confirmed when the process was reproduced. Thus when the process was carried out in analogous manner starting from 2-(2'-aminophenyl)ethanol, after a reaction time of 2.75 hours and at a reaction temperature of 250° C., the conversion was only 2.4%, corresponding to a yield of 1% of theory in a selectivity of 42%. After the same reaction time of 2¾ hours and at a temperature of 280° C., the conversion was 5.5%, the selectivity 38% and the yield 2.1% of theory. After a reaction time of 7 hours and at a reaction temperature of 300° C., the conversion was 18.3%, the selectivity 83% and the yield 15.3% of theory. Using specially purified 2-(2'-aminophenyl)ethanol (99.9%) and carrying out the reaction in a purified glass apparatus, the conversion was only 0.5% after a reaction time of 2 hours and at a temperature of 250° C.

Published Japanese patent application No. 58-146.563 describes a process wherein the cyclodehydration of 2-(2'-aminophenyl)ethanol to indoline is carried out in liquid phase in the temperature range of 200°-220° C. in the presence of phosphoric acid, boric anhydride, sulfuric acid or nitric acid on γ-alumina as carrier, or in the presence of phosphoric acid, boric acid or boric anhydride on titanium dioxide as carrier. In this process, employing a catalyst consisting of γ-alumina and sulfuric acid and which is used in an amount of 10% by weight, based on 2-(2'-aminophenyl)ethanol, indoline is obtained in a yield of 96.3% of theory and in 97.7% purity after a reaction time of 1½ hours and at a reaction temperature of 216°-218° C. A substantial drawback of this process is that large amounts of catalyst are required to achieve a satisfactory reaction rate.

Finally, Japanese patent application No. SHO 58-146.562 discloses a process for the preparation of indoline, wherein gaseous 2-(2'-aminophenyl)ethanol is passed at 180°-300° C. over a catalyst that consists of alumina or silica gel which is impregated with a boron or phosphorus compound, preferably boric acid or phosphoric acid respectively. This process is disadvantageous in that the catalyst is rapidly deactivated. Moreover, the process has to be worked under reduced pressure which requires a rather complicated and expensive apparatus.

In a process described in British patent application No. 2 501 065 A, indolines are prepared by heating suitable 2-(2'-aminophenyl)ethanol hydrohalides, in liquid phase, to temperatures above 120° C. In this process, the liquid phase may be formed by the melt of the hydrohalide employed or by an aqueous solution thereof. A considerable drawback of this process is that the desired indolines are not obtained in the free form but in the form of their hydrohalides, from which they have to be set free and isolated in a further process step.

It is the object of the present invention avoid the disadvantages of the known processes and to provide a process in which the indolines of formula I can be obtained direct in good yield by cyclodehydration of 2-(2'-aminophenyl)ethanol of formula II.

It has now been found that the indolines of formula I can be prepared in excellent yield by cyclodehydrating a 2-(2'-aminophenyl)ethanol of formula II by carrying out the cyclodehydration of said 2-(2'-aminophenyl)ethanol of formula II at 150°–350° C. in the presence of an amorphous aluminium silicate. The process according to the invention can be carried out in the gaseous phase as well as in the liquid phase.

Particularly suitable aluminium silicates in the presence of which the process of this invention is carried out are those consisting of 5–30% by weight of $Al_2O_3$ and 70–95% by weight of $SiO_2$ and having a BET inner surface area of 50–800 m$^2$/g and a pore volume of 0.3–1.0 cm$^3$/g. It is preferred to use amorphous aluminium silicates consisting of 10–20% by weight of $Al_2O_3$ and 80–90% by weight of $SiO_2$ and having a BET inner surface area of 300–600 m$^2$/g and a pore volume of 0.4–0.7 cm$^3$/g. Particularly preferred amorphous aluminium silicates are those consisting of 10–15% by weight of $Al_2O_3$ and 85–90% by weight of $SiO_2$ and having a BET inner surface area of 300–500 m$^2$/g and a pore volume of 0.5–0.7 cm$^3$/g. The percentages of aluminium oxide ($Al_2O_3$) and silicon dioxide relate to the amount of these components assessable as solid oxides by analysis of the amorphous aluminium silicates to be used according to the invention.

The amorphous aluminium silicates which are eligible for use as catalysts in the process of this invention may generally be obtained by adding an aqueous solution of an aluminium salt, for example sodium silicate, isolating the precipitate by filtration, and washing and calcining the filter product. The preparation of the catalysts can also be effected by precipitating silica gel form an aqueous solution of sodium silicate by addition of sulfuric acid, and adding aluminium sulfate and ammonia to said silica gel after a certain period of ageing, while keeping the pH in the weakly acidic range. The precipitate is then isolated by filtration, washed, dried and calcined. The preparation of the catalysts eligible for use in this invention is described e.g. in U.S. patent specification Nos. 2 283 172 and 2 283 173. Additional information on the structure of the amorphous aluminiumsilicates which are used according to the present invention can be obtained from an article published in End. Eng. Chem. 41 (1949), pages 2564–73.

Amorphous aluminium silicates suitable for use as catalysts in the process of the present invention are also commercially available, for example under the registered trademark KETJEN ® LA-100-3P (Akzo Chemie, Amsterdam) and HOUDRY-HUELS S-90 (Chemische Werke Hüls AG).

According to a preferred embodiment of the present invention the indolines of the formula I are obtained in excellent yield by carrying out the cyclodehydration of a 20(2'-aminophenyl)ethanol of formula II at 200°–300° C. in the gaseous phase in the presence of an amorphous aluminium silicate consisting of 5–30% by weight of $Al_2O_3$ and 70–95% by weight of $SiO_2$ and having a BET inner surface area of 50–800 m$_2$/g and a pore volume of 0.1–1.0 cm$^3$/g.

Within the indicated range of 200°–300° C., reaction temperatures of 240°–260° C. are preferred.

The process of this invention is conveniently carried out in the gaseous phase at a throughput of 0.1 to 10 kg of 2-(2'-aminophenyl)ethanol of formula II per kilogram of catalyst and per hours. It is preferred to carry out the process at a throughput of 0.5 to 2 kg of 2-(2'-aminophenyl)ethanol per kilogram of catalyst and per hour.

It is also advantageous to carry out the process in the gaseous phase in the presence of a carrier gas. Suitable carrier gases are for example nitrogen, hydrogen and steam. It is preferred to carry out the process of the present invention in the presence of steam as carrier gas.

The carrier gas is normally employed in an amount of 1–10 moles per mole of 2-(2'-aminophenyl)ethanol of formula II. Preferably 6–8 moles of carrier gas are employed per mole of 2-(2'-aminophenyl)ethanol of formula II.

The mixtures of carrier gas and gaseous 2-(2'-aminophenyl)ethanol of formula II are conveniently prepared by adding the respective carrier gas to the gaseous 2-(2'-aminophenyl)ethanol. When using steam as carrier gas, it is advantageous to evaporate an aqueous solution of 2-(2'-aminophenyl)ethanol of formula II. Particularly suitable aqueous solutions are those containing 40–60% by weight of 2-(2'-aminophenyl)ethanol of formula II.

The catalysts eligible for use in the process of this invention can be used in a fixed bed, for example in a tube reactor, or in a fluidised bed, for example in a fluidised bed reactor. In a fixed bed the amorphous aluminium silicates are advantageously used in the form of pellets.

The pressure under which the process of the invention is carried out is not crucial. It is preferred to carry out the process under normal pressure. However, the process may also be carried out under vacuum or excess pressure, in which case it must be ensured that the reaction mixture is in gaseous form by suitable choice of reaction temperature and by using a carrier gas.

According to another preferred embodiment of the present invention the indolines of the formula I are obtained in excellent yield by carrying out the cyclodehydration of a 2-(2'-aminophenyl)ethanol of formula II at 150°–350° C. in liquid phase in the presence of an amorphous aluminium silicate consisting of 5–30% by weight of $Al_2O_3$ and 70–95% by weight of $SiO_2$ and having a BET inner surface area of 50–800 m$^2$/g and a pore volume of 0.1–1.0 cm$^3$/g.

Within the indicated range of 150°–350° C., reaction temperatures of 200°–280° C. are preferred.

The liquid phase process of this invention can be carried out discontinuously in single batches or continuously. It is preferred to carry out the process continuously.

The discontinuous method preferably comprises suspending the amorphous aluminium silicate in the starting 2-(2'-aminophenyl)ethanol of formula II and heating the suspension to 150°–350° C., preferably to 200°–280° C., with the pressure being chosen such that it is above the vapour pressure generated by the reaction mixture at the reaction temperature. A stirred autoclave is preferably employed as reactor. Depending on the reaction temperature and the amount of catalyst, the reaction time is from ½ hour to 3 hours. When the reaction is complete, the reaction mixture is worked up by fractional distillation. As the reaction to the indoline of formula I is usually almost quantitative, it generally suffices to remove the water of reaction by distillation and to separate the catalyst to obtain a product that is suitable for most purposes. The product obtained after separating off the water of reaction and the catalyst can, if desired, also be purified by distillation in order to remove high-boiling by-products that are always formed in small amounts during the reaction. In an advantageous process variant, the water of reaction is distilled off during the reaction itself. In this case, the reaction is performed under a pressure that is above the vapour pressure generated at the respective reaction temperature of starting and final product. The desired indolines are thus obtained direct upon completion of the reaction and separation of the amorphous aluminium silicate.

The continuous method preferably comprises heating the 2-(2'-aminophenyl)ethanol of formula II and the amorphous aluminium silicate in a reactor equipped with a stirrer, metering means and a distillation column to reaction temperature, at a pressure equivalent to the vapour pressure of the reaction mixture at the chose reaction temperature, distilling off the reaction products, viz. water and indoline of formula I, through the column, and constantly adding to the reaction mixture, via the metering means, an amount of fresh 2-(2'-aminophenyl)ethanol of formula II commensurate with the amount of water and indoline removed by distillation. The rate of distillation and the rate of addition corresponding thereto are conveniently chosen such that the average residence time in the reactor is from ½ hour to 3 hours, depending on the chosen reaction temperature and on the amount of catalyst employed.

As small amounts of high-boiling by-products are always formed during the cyclodehydration of 2-(2'-aminophenyl)ethanol of formula II under the conditions of liquid phase process, the boiling point of the reaction mixture rises with increasing reaction time when carrying out the process continuously. To maintain a constant reaction rate despite this rise in boiling point, it is therefore necessary either constantly to increase the reaction temperature commensurately or constantly to reduce the pressure commensurately. If the proportion of high-boiling by-products in the reaction mixture is too high, then they must be removed. This removal can be simply accomplished by discontinuing the addition of 2-(2'-aminophenyl)ethanol of formula II, distilling off the indoline of formula I present in the reaction mixture from the reactor, separating the high-boiling products present in the distillation residue from amorphous aluminium silicate by filtration, and commencing a new cycle with the same or with fresh amorphous aluminium silicate.

The amount of amorphous aluminium silicate is normally 0.5 to 10% by weight, based on 2-(2'-aminophenyl)ethanol, in the discontinuous method, and 0.5 to 10% by weight, based on the amount of reaction mixture present in the reactor in the continuous method. It is preferred to use the amorphous aluminium silicate in an amount of 1-5% by weight, based on 2-(2'-aminophenyl)ethanol of formula II, in the discontinuous method, and in an amount of 1-5% by weight, based on the amount of reaction mixture present in the reactor, in the continuous method.

The starting 2-(2'-aminophenyl)ethanols of formula II can be prepared in a manner known per se by reacting suitable 2-nitroalkylbenzenes with aliphatic and aromatic aldehydes and subsequently reducing the 2-(2'-nitrophenyl)ethanols so obtained. The reaction of 2-nitroalkylbenzenes with aliphatic or aromatic aldehydes is described e.g. in published Japanese patent application No. 77.108.941. The reduction of 2-(2'-nitrophenyl)ethanols can be carried out in accordance with Bull. Soc. Chim. France, (1931), 49, page 3, with zinc.

The process of the present invention is particularly suitable for the preparation of indoline. Hence the preferred starting material is 2-(2'-aminophenyl)ethanol. A preferred variant of the process of the invention comprises the preparation of indoline by cyclodehydrating 2-(2'-aminophenyl)ethanol at 240°–260° C., in the gaseous phase in the presence of an amorphous aluminium silicate consisting of 10–15% by weight of $Al_2O_3$ and 85–90% by weight of $SiO_2$ and having a BET inner surface area of 300–500 m$^2$/g and a pore volume of 0.5–0.7 cm$^3$/g, as catalyst, and in the presence of 6–8 moles of steam per mole of 2-(2'-aminophenyl)ethanol, with the throughput of 2-(2'-aminophenyl)ethanol being 0.5 to 2 kg per kilogram of catalyst and per hour.

According to another preferred variant of the process according to the invention comprises the preparation of indoline by cyclodehydrating 2-(2'-aminophenyl)-ethanol in liquid phase in the presence of 1–5% by weight calculated on the total weight of the reaction mixture of an amorphous aluminium silicate consisting of 10–15% by weight of $Al_2O_3$ and 85–90% by weight of $SiO_2$ and having a BET inner surface of 300–500 m$^2$/g and a pore volume of 0.5–0.7 cm$^3$/g at an average residence time of 0.5–3 hours.

A conversion of 98–100% of 2-(2'-aminophenyl)ethanol of formula II is achieved with the process of this invention, with the indolines of formula I being obtained in a selectivity of up to 98–99%. The particular advantage of the process of this invention is that the amorphous aluminium silicates which are used as catalysts according to the present invention remain active over a substantially longer period of time compared with the catalysts used hitherto for the cyclodehydraton of 2-(2'-aminophenyl)ethanols. Compared to the process carried out in the gaseous phase the liquid phase process offers the advantage of a better yield per volume.

The following Examples illustrate the process of the invention in more detail.

EXAMPLE 1

In a Pyrex glass tube reactor with an internal diameter of 28 mm, 8.3 g/h of 2-(2'-aminophenyl)ethanol and 8.3 g/h of steam are passed at 250° C. over 15.0 g of a pelleted amorphous aluminium silicate consisting of 13.5% by weight of $Al_2O_3$ and 86% by weight of $SiO_2$ and having a BET inner surface area of 418 m$^2$/g and a pore volume of 0.51 cm$^3$/g (KETJEN ® LA-100-3P, ex Akzo Chemie, Amsterdam). After an operating time of 1500 hours, a 98–100% conversion of 2-(2'-aminophenyl)ethanol to indoline is achieved, with the indoline being obtained in a selectivity of 98–99%. The 98–100% conversion of 2-(2'-aminophenyl)ethanol remains unchanged at the conclusion of the experiment.

EXAMPLE 2

In a Pyrex glass tube reactor with an internal diameter of 28 mm, 18.9 g/h of a gas mixture obtained by evaporating a 50% aqueous solution of 2-(2'-aminophenyl)ethanol are passed at 250° C. over 8.6 g of an amorphous aluminium silicate consisting of 12.4% by weight of $Al_2O_3$ and 87.3% by weight of $SiO_2$ and having a BET inner surface area of 317 m$^2$/g and a pore volume of 0.64 cm$^3$/g (HOUDRY-HüIS s-90). After an operating time of 730 hours without intermediate regeneration of the catalyst, a 98-100% conversion of 2-(2'-aminophenyl)ethanol to indoline is achieved, with the indoline being obtained in a selectivity of 98-99%. No reduction in conversion is observed at the conclusion of the experiment.

EXAMPLE 3

In a stainless steel reactor equipped with distillation column, 5.0 g of a commercially available amorphous aluminium silicate (KETJEN ® C-25-W) consisting of 14.7% by weight of $AL_2O_3$ and 82.5% by weight of $SiO_2$, and having a BET inner surface area of 547 m$^2$/g and a pore volume of 0.61 cm$^3$/g, are suspended in 130 g (117 ml) of 2-(2'-aminohenyl)ethanol using a magnetic stirrer. The suspension is heated to 220° C. Then, at a constant reaction temperature of 220° C. and under an initial pressure of 0.5 bar, the resultant indoline/water mixture is distilled off through the packed column at an average rate of 60 g of indoline per hour. During this distillation, the volume in the reactor is kept constant with a level probe by the continuous addition of fresh 2-(2'-aminophenyl)ethanol. The reduction in the distillation rate caused by the formation of high-boiling by-products is compensated for by gradually lowering the pressure for maintaining the distillation rate over the duration of the experiment form 0.5 to 0.07 bar. After a reaction time of 150 hours, the addition of 2-(2'-aminophenyl)ethanol is discontinued and the indoline present in the reactor is distilled off under reduced pressure affording 9.0 kg of indoline in 99.5% purity as distillate. 55 g of high-boiling by-products of unknown constitution are obtained as distillation residue. The yield of indoline is 98-99% of theory.

EXAMPLE 4

In a stainless steel reactor equipped with distillation column, 0.8 g of a commercially available amorphous aluminium silicate (KETJEN ® LA-100-3P) consisting of 13.3% by weight of $Al_2O_3$ and 86.3% by weight of $SiO_2$, and having a BET inner surface area of 403 m$^2$/g and a pore volume of 0.52 cm$^3$/g, are suspended in 80 g (72 ml) of 2-(2'-aminophenyl)ethanol using a magnetic stirrer. The suspension is heated to 240° C. under normal pressure and the resultant indoline/water mixture is distilled off through the packed column at a rate of 25 g of indoline per hour. During this distillation, the volume in the reactor is kept constant with a level probe by the continuous addition of fresh 2-(2'-aminophenyl)ethanol. To maintain this distillation rate, the reaction temperature is gradually raised during the entire duration of the experiment of 126 hours from initially 240° C. to 270° C. After 126 hours, the addition of 2-(2'-aminophenyl)ethanol is discontinued and the indoline remaining in the reactor is distilled off through the column, affording 2.95 kg (97-98% of theory) of indoline in 99% purity.

What is claimed is:

1. A process for the preparation of indolines of the formula

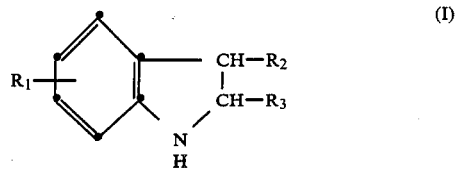

wherein $R_1$ is hydrogen of $C_1$–$C_4$alkyl and each of $R_2$ and $R_3$ independently of the other is hydrogen, $C_1$–$C_4$alkyl or phenyl, by cyclodehydrating a 2-(2'-aminophenyl)ethanol of the formula

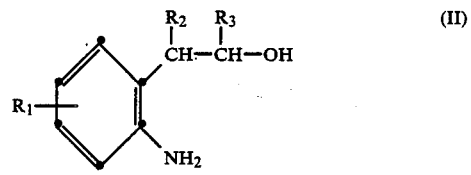

wherein $R_1$, $R_2$ and $R_3$ are as defined for formula I, in the presence of a catalyst, which process comprises carrying out the cyclodehydration of said 2-(2'-aminophenyl)ethanol of formula II in the presence of an amorphous aluminum silicate which is substantially free of other metal ions, wherein the temperature is 200°-300° C. and the throughput of the 2-(2'-aminophenyl)ethanol of formula II is 0.1 to 10 kg per kg of said amorphous aluminum silicate and per hour when said process is carried out in the gaseous phase or wherein the temperature is 150°-350° C. and the amorphous aluminium silicate is used in an amount of 0.5 to 10% by weight, based on 2-(2'-aminophenyl)ethanol of formula II when carried out discontinuously and 0.5 to 10% by weight, based on the amount of reaction mixture present in the reactor when carried out continuously in the liquid phase.

2. A process according to claim 1, which comprises carrying out the cyclodehydration of said 2-(2'-aminophenyl)ethanol of formula II at 200°-300° C. in the gaseous phase in the presence of an amorphous aluminium silicate consisting of 5-30% by weight of $Al_2O_3$ and 70-95% by weight of $SiO_2$ and having a BET inner surface area of 50-800 m$^2$/g and a pore volume of 0.1-1.0 cm$^3$/g, the throughout of the 2-(2'-aminophenyl)ethanol of the formula II being 0.1 to 10 kg per kg of catalyst and per hour.

3. A process according to claim 2, wherein the cyclodehydration of 2-(2'-aminophenyl)ethanol of formula II is carried out at 240°-260° C.

4. A process according to claim 2, wherein the catalyst employed is an amorphous aluminium silicate consisting of 10-20% by weight of $Al_2O_3$ and 80-90% by weight of $SiO_2$ and having a BET inner surface area of 300-600 m$^2$/g and a pore volume of 0.4-0.7 cm$^3$/g.

5. A process according to claim 4, wherein the catalyst employed is an amorphous aluminium silicate consisting of 10-15% by weight of $Al_2O_3$ and 85-90% by weight of $SiO_2$ and having a BET inner surface area of 300-500 m$^2$/g and a pore volume of 0.5-0.7 cm$^3$/g.

6. A process according to claim 2, wherein the throughput of 2-(2'-aminophenyl)ethanol of formula II is 0.5 to 2 kg per kilogram of catalyst and per hour.

7. A process according to claim 2, wherein the cyclodehydration of 2-(2'-aminophenyl)ethanol of formula II is carried out in the presence of a carrier gas.

8. A process according to claim 7, wherein the carrier gas is nitrogen, hydrogen or steam.

9. A process according to claim 7, wherein the carrier gas is steam.

10. A process according to claim 7, wherein 1 to 10 moles of carrier gas are used per mole of 2-(2'-aminophenyl)ethanol of formula II.

11. A process according to claim 7, wherein 6 to 8 moles of carrier gas are used per mole of 2-(2'-aminophenyl)ethanol of formula II.

12. A process according to claim 2, which comprises cyclodehydrating 2-(2'-aminophenyl)ethanol.

13. A process according to claim 12, which comprises cyclodehydrating 2-2(2'-aminophenyl)ethanol at 240°–260° C. in the presence of an amorphous aluminium silicate consisting of 10–15% by weight of $Al_2O_3$ and 85–90% by weight of $SiO_2$ and having a BET inner surface area of 300–500 $m^2/g$ and a pore volume of 0.5–0.7 $cm^3/g$, as catalyst, and in the presence of 6 to 8 moles of steam per mole of 2-(2'-aminophenyl)ethanol, at a throughput of 2-(2'-aminophenyl)ethanol 0.5 to 2 kg per kilogram and per hours.

14. A process according to claim 1, which comprises carrying out the cyclodehydration of said 2-(2'-aminophenyl)ethanol of formula II at 150°–350° C. in the liquid phase in the presence of an amorphous aluminium silicate consisting of 5–30 % by weight of $Al_2O_3$ and 70–95% by weight of $SiO_2$ and having a BET inner surface area of 50–800 $m^2/g$ and a pore volume of 0.1–1.0 $cm^3/g$ and wherein the amorphous aluminium silicate is used in an amount of 0.5 to 10% by weight, based on 2-(2'-aminophenyl)ethanol of formula II when carried out discontinuously and 0.5 to 10% by weight, based on the amount of reaction mixture present in the reactor when carried out continously.

15. A process according to claim 14, wherein the cyclodehydration of 2-(2'-aminophenyl)ethanol of formula II is carried out at 200°–280° C.

16. A process according to claim 14, which comprises carrying out the cyclodehydration of the 2-(2'-aminophenyl)ethanol of formula II in the presence of an amorphous aluminium silicate consisting of 10–20% by weight of $Al_2O_3$ and 80–90% by weight of $SiO_2$ and having a BET inner surface area of 300–600 $m^2/g$ and a pore volume of 0.4–0.7 $cm^3/g$.

17. A process according to claim 14, which comprises carrying out the cyclodehydration of the 2-(2'-aminophenyl)ethanol of formula II in the presence of an amorphous aluminium silicate consisting of 10–15% by weight of $Al_2O_3$ and 85–90% by weight of $SiO_2$, and having a BET inner surface area of 300–500 $m^2/g$ and a pore volume of 0.5–0.7 $cm^3/g$.

18. A process according to claim 14 which is carried out continuously or discontinuously.

19. A process according to claim 18 which is carried out continuously.

20. A process according to claim 14, wherein the reaction time is 0.5–3 hours.

21. A process according to claim 14, wherein the amorphous aluminium silicate is used in an amount of 1–5% by weight, based on the amount of reaction mixture present in the reactor.

22. A process according to claim 14, which comprises cyclodehydrating 2-(2'-aminophenyl)ethanol.

23. A process according to claim 22, which comprises cyclodehydrating 2-(2'-aminophenyl)-ethanol at 200°–280° C. in liquid phase in the presence of 1–5% by weight calculated on the total weight of the reaction mixture of an amorphous aluminium silicate consisting of 10–15% by weight of $Al_2O_3$ and 85–90% by weight of $SiO_2$ and having a BET inner surface of 300–500 $m^2/g$ and a pore volume of 0.5–0.7 $cm^3/g$ at a reaction time of 0.5–3 hours.

* * * * *